(12) United States Patent
Chung

(10) Patent No.: US 9,440,035 B2
(45) Date of Patent: Sep. 13, 2016

(54) VAPOR INHALER

(71) Applicant: Henry Chung, Walnut, CA (US)

(72) Inventor: Henry Chung, Walnut, CA (US)

( * ) Notice: Subject to any disclaimer, the term of this patent is extended or adjusted under 35 U.S.C. 154(b) by 359 days.

(21) Appl. No.: 14/044,045

(22) Filed: Oct. 2, 2013

(65) Prior Publication Data

US 2015/0090256 A1   Apr. 2, 2015

(51) Int. Cl.
| | |
|---|---|
| *A24F 5/04* | (2006.01) |
| *A61M 15/00* | (2006.01) |
| *A61M 15/06* | (2006.01) |
| *A24F 47/00* | (2006.01) |
| *A61M 11/04* | (2006.01) |

(52) U.S. Cl.
CPC .......... *A61M 15/002* (2014.02); *A24F 47/004* (2013.01); *A24F 47/008* (2013.01); *A61M 11/042* (2014.02); *A61M 15/06* (2013.01); *A61M 15/0021* (2014.02); *A61M 2205/8206* (2013.01)

(58) Field of Classification Search
CPC .. A24F 47/002; A24F 47/004; A24F 47/006; A24F 47/008; A61M 11/042; A61M 15/0021; A61M 15/06; A61M 2205/8206
USPC ........... 131/198.1, 198.2, 206, 215.1, 215.2, 131/215.3, 223
See application file for complete search history.

(56) References Cited

U.S. PATENT DOCUMENTS

2007/0079839 A1* 4/2007 Russon .................... A24F 1/30 131/173
2013/0152922 A1* 6/2013 Benassayag .......... A61M 15/06 128/202.21

* cited by examiner

*Primary Examiner* — Peter S Vasat
(74) *Attorney, Agent, or Firm* — Clement Cheng

(57) ABSTRACT

A vapor inhaler includes a handle with a battery. A heater is connected to the handle and the heater has heater air intake openings for receiving air. The heater has heater air conduits for exhausting air. A cartridge housing is connected to the heater. The cartridge housing has a cartridge housing lid and a cartridge housing lid grille mounted to the cartridge housing lid. The cartridge housing produces vapor. A main body is connected to the cartridge housing, and the main body further includes a mouthpiece. A regulator valve is mounted to the main body. The regulator valve has a regulator valve secondary opening that provides a supplemental ambient air supply when the regulator valve is in an open position. The regulator valve does not provide a supplemental ambient air supply when the regulator valve is in closed position.

16 Claims, 2 Drawing Sheets

VAPOR INHALER

FIELD OF THE INVENTION

The present invention is in the field of vapor inhalers.

DISCUSSION OF RELATED ART

Smokers are addicted to nicotine found inside cigarettes. However, nicotine is only one reason why cigarettes are harmful. Cigarettes also contain tar and consist of other carcinogenic ingredients that contribute to the overall decline on human health with prolonged usage. Smokers also endanger surrounding people when they smoke. After inhaling then exhaling on a cigarette, the air exhaled comprises of more than carbon monoxide. Remnants of the cigarette's carcinogenic components linger in the air for a passerby to involuntarily inhale. Fortunately, regulations exist to reduce such occurrences and smoking in public area has mostly been prohibited in developed countries.

With social pressure to quit smoking and the devastating side effects of smoking, users have sought several methods to reduce or cease their habit. Some common methods include the usage of nicotine patches or nicotine gum to curb nicotine cravings. Therapy and support groups also exist to provide encouragement throughout the process. More recently is the invention of vapor inhalers configured as electronic cigarettes that contain nicotine, which proposes to help ease users off real cigarettes by simulating the appearance, feel, and pleasure derived from smoking. A variety of different vapor inhalers have been used for allowing a user to inhale vapor such as Lik Hon, U.S. Pat. No. 8,511,318, issued on Aug. 20, 2013, entitled Electronic Cigarette disclosed herein by reference. Hon teaches about a vapor inhaler that includes a shell, a cell, nicotine solution, control circuit, and an electro-thermal vaporization nozzle installed in the air suction of the end shell; stating the advantages of which include smoking without tar, reducing cancer risk, simulation of smoking experience, and no fire danger since the cigarette is not lit. Another example of vapor inhalers is Tucker et al., U.S. 2013/0192620, issued Aug. 1, 2013, entitled Electronic Cigarette disclosed herein by reference. Tucker discloses an electronic smoking article that includes a heater operable to heat liquid material, a wick to deliver the liquid material to the heater, an inlet to deliver air, and a fibrous element downstream of the heater.

To greater enhance the simulation of smoking other types of vapor inhalers enable users to add flavoring agents such as tobacco flavor or menthol. Kyle Newton, U.S. 2013/0228191, issued on Sep. 5, 2013, entitled Electronic Cigarette with Liquid Reservoir disclosed herein by reference. Newton introduces an elongated housing that serves as a liquid reservoir chamber, which proposes to extend the duration in between time when users would need to change a flavoring cartridge.

Vapor inhalers also seek to emulate other aspects of a real cigarette. Mark Scatterday, U.S. Pat. No. 8,539,959, issued on Sep. 24, 2013, entitled Electronic Cigarette Configured to Simulate the Natural Burn of a Cigarette disclosed herein by reference. Scatterday proposes an electronic cigarette which may have a translucent conduit and light chamber, allowing light from the light source to be diffused in such a way that the light emitted during inhalation simulates the natural burn of a traditional tobacco cigarette.

The present inventions seeks to enable users the ability to regulate the amount of vapors inhaled in one breath, which has not yet been demonstrated by prior art. This ability also allows a multitude of users, who are most likely on different stages of quitting, to adjust to an amount of smoking that is appropriate to their individual needs.

SUMMARY OF THE INVENTION

A vapor inhaler includes a handle with a battery. A heater is connected to the handle and the heater has heater air intake openings for receiving air. The heater has heater air conduits for exhausting air. A cartridge housing is connected to the heater. The cartridge housing has a cartridge housing lid and a cartridge housing lid grille mounted to the cartridge housing lid. The cartridge housing produces vapor that passes through the cartridge housing lid grille. A main body is connected to the cartridge housing, and the main body further includes a mouthpiece. A regulator valve is mounted to the main body. The regulator valve has a regulator valve secondary opening that provides a supplemental ambient air supply when the regulator valve is in an open position. The regulator valve does not provide a supplemental ambient air supply when the regulator valve is in closed position.

The regulator valve has a regulator valve secondary opening located on a regulator valve switch. The regulator valve switch is formed as a pushbutton. The regulator valve secondary opening is located on a sidewall of the pushbutton. The main body further includes a main body cartridge housing cavity. The cartridge housing is mounted to fit within the main body cartridge housing cavity. The vapor inhaler optionally has the mouthpiece detachable from the main body. The main body has a main body secondary outlet that has fluid communication to ambient air when the regulator valve is in open position. The main body has a main body vapor outlet providing a flow of vapor.

The main body further includes a main body regulator valve cavity. The regulator valve is mounted to fit within the main body regulator valve cavity. The regulator valve has a regulator valve body narrow portion sized to provide a conduit of vapor flow through the main body from a main body cartridge housing cavity to the mouthpiece. The regulator valve has a regulator valve body fitting portion, and the regulator valve has a fitting portion with a regulator valve seal that is formed as an O-ring to seal against an inside surface of the main body regulator valve cavity.

It is an object of the invention to improve the design of the vapor inhaler.

The following call out list of elements can be a useful guide in referencing the elements of the drawings.

20 Handle
21 Switch
22 Battery Cover
23 Switch Light
24 Battery
25 Ventilation Opening
26 Handle Connector Face
27 First Polarity Terminal Of The Handle
28 Second Polarity Terminal Of The Handle
30 Heater
31 Heater Sidewall
32 Heater Recess
33 Second Polarity Terminal Of The Heater 34 First Polarity Terminal Of The Heater
35 Heater Air Intake Opening
36 Heater Threaded Connection
37 Heater Air Conduits
38 Heater Coil Element
40 Cartridge Housing
41 Cartridge Housing Outside Wall
42 First Cartridge Housing O-Ring Seal Groove
43 Second Cartridge Housing O-Ring Seal Groove
44 Cartridge Housing Chamber
50 Cartridge Housing Lid
51 Cartridge Housing Lid Sidewall
52 Cartridge Housing Lid Threaded Connection
53 Cartridge Housing Lid Grille
60 Grille Baffle Plate
61 Grille Baffle Plate Rim
62 Grille Baffle Plate Apertures
70 Regulator Valve
71 Regulator Valve Switch
72 Regulator Valve Secondary Opening
73 Regulator Valve Seal
74 Regulator Valve Body Fitting Portion
75 Regulator Valve Body Narrow Portion
76 Regulator Valve Intake Opening
80 Main Body
81 Main Body Cartridge Housing Cavity
82 Main Body Regulator Valve Cavity
83 Main Body Regulator Valve Cavity Air Outlet
84 Main Body Mouthpiece O-Ring Seal
85 Main Body Secondary Outlet
86 Main Body Vapor Outlet
87 Main Body Sidewall Rim
88 Main Body Sidewall
89 Main Body Mouth Piece Mesa
90 Mouth Piece
91 Mouthpiece Flare
92 Mouthpiece Rim
93 Mouthpiece Channel

DETAILED DESCRIPTION OF THE PREFERRED EMBODIMENT

Figure 1:
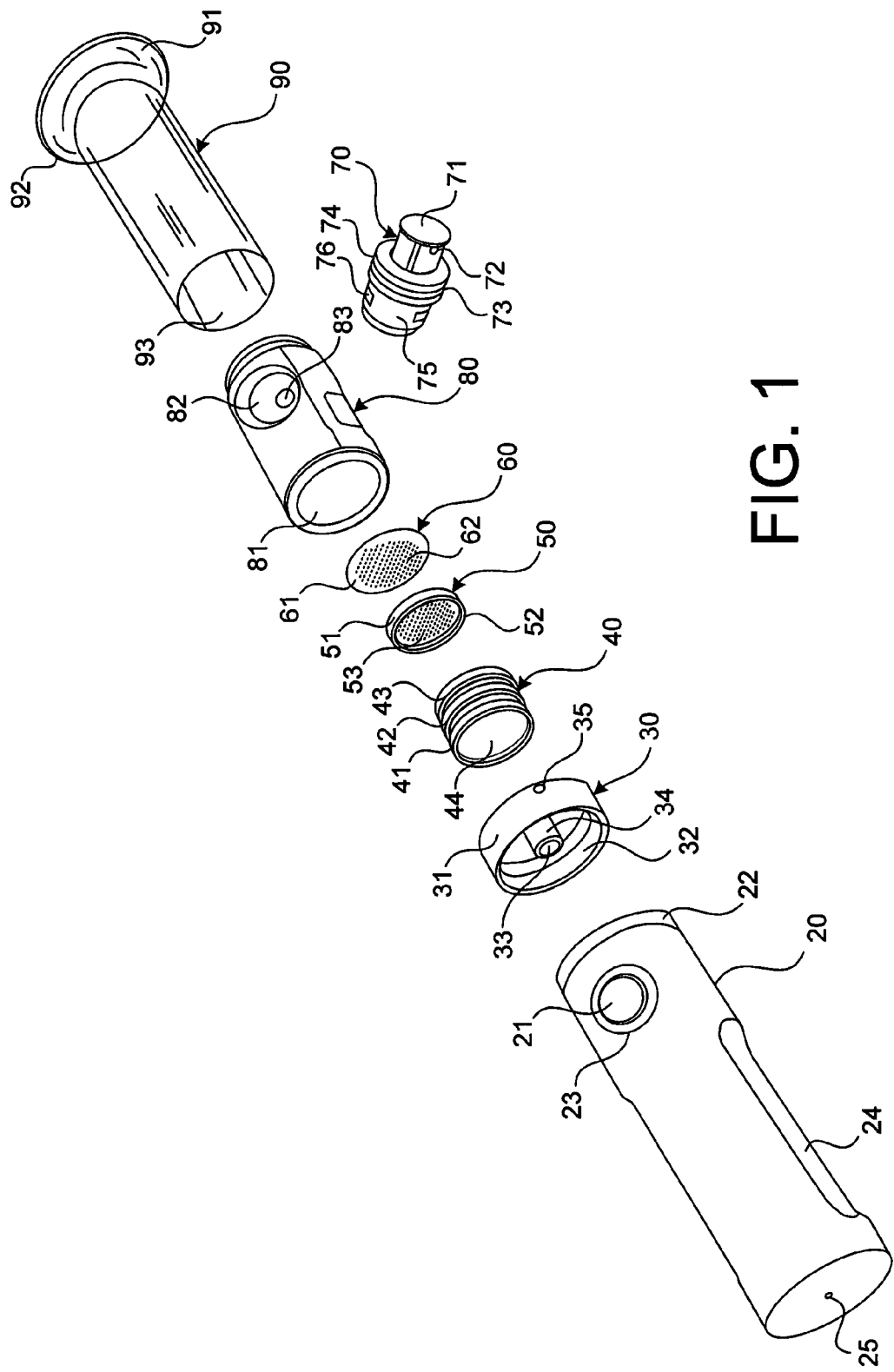
FIG. 1 is a rear exploded view of the present invention showing assembly.
Figure 2:
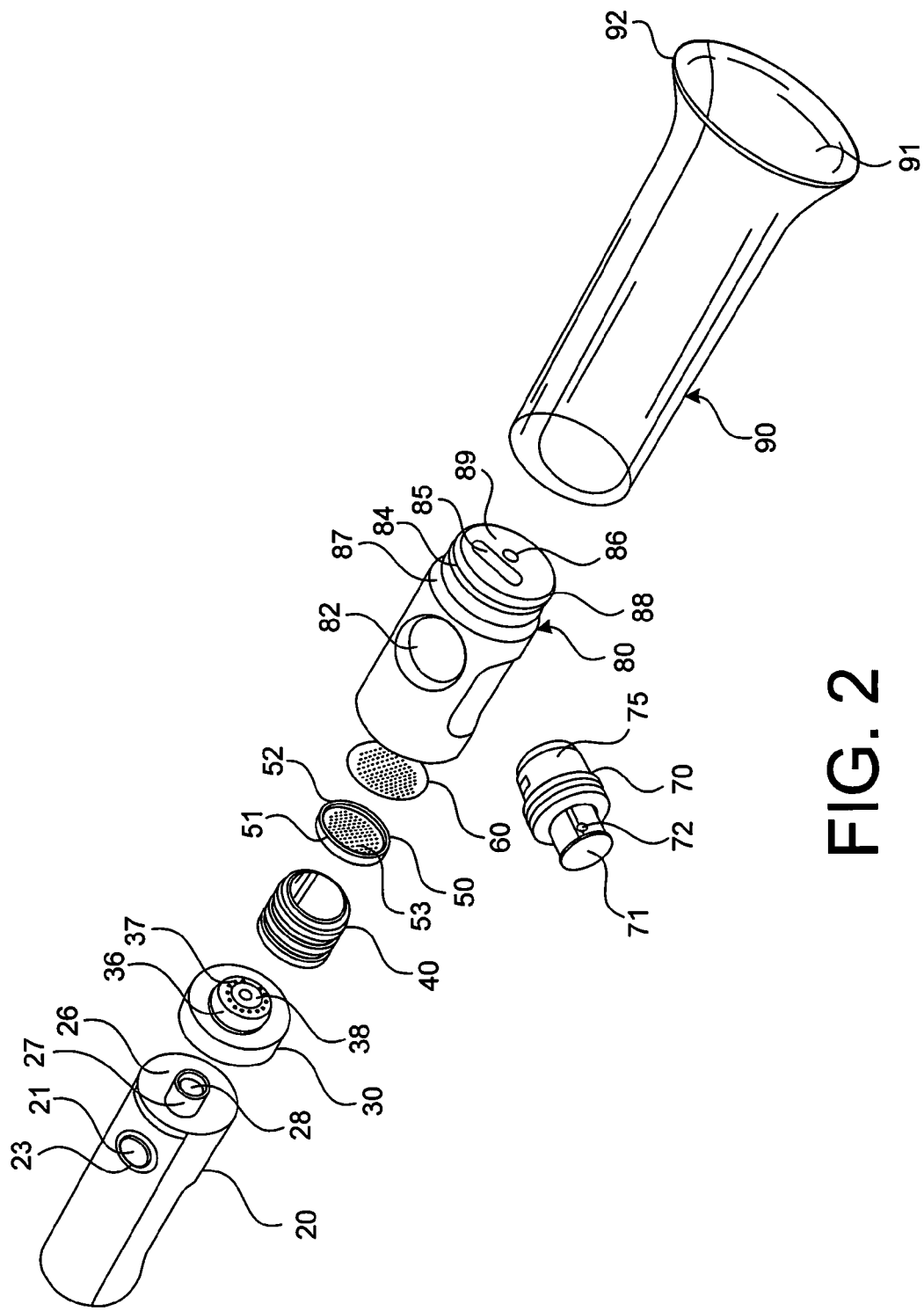
FIG. 2 is a front exploded view of the present invention vapor inhaler showing assembly.

FIGS. 1, 2 show an exploded view of the present invention. The handle 20 contains a battery 24 and has a ventilation opening 25 on a lower end of the handle 20. The handle 20 also includes an electronic switch 21 which can be configured as a pushbutton with a switch light 23. The switch light 23 can be a multiple color LED that is activated when the pushbutton is depressed by a user. When the pushbutton is depressed, the battery provides electrical power for a predetermined amount of time. The battery is retained within the handle by the battery cover 22. The handle 20 is a power supply that can be made in a cylindrical shape. The handle can be made of metal.

The handle also includes a handle connector face 26 that connects to the heater 30. The handle connector face may have a plurality of terminals including a first polarity terminal of the handle 27 and a second polarity terminal of the handle 28. The first polarity could be a negative or positive polarity and the second polarity can be a negative or positive polarity. The polarity can be AC or DC power. Preferably, low voltage DC power is desired. The first polarity terminal of the handle 27 is shown as a raised stem. Insulated from the first polarity terminal of the handle 27 is a second polarity terminal of the handle 28. The second polarity terminal of the handle 28 is shown as a metal plate that is located within the raised stem. The metal plate can be spring mounted to have spring biased. The raised stem of the first polarity terminal of the handle 27 can have a threaded internal or external surface. The threaded internal or external surface can connect to a threaded internal or external surface located on the heater.

The heater 30 can be formed as an atomizer. The heater can be made in a cylindrical shape with a heater recess 32 to define a protruding stem. The heater generally includes a heater sidewall 31. The heater sidewall 31 may have a plurality of heater air intake openings 35. The heater has a first polarity terminal of the heater 34, and a second polarity terminal of the heater 33. The first polarity terminal of the heater 34 is insulated from the second polarity terminal of the heater 33. The first polarity terminal of the heater 34 makes electrical connection with the first polarity terminal of the handle 27, and makes mechanical connection where the first polarity terminal of the heater 34 has an external threaded surface that engages an internal threaded surface of the first polarity terminal of the handle 27. The first polarity terminal of the handle 27 is formed as a first stem, and the first polarity terminal of the heater 34 is formed as a second stem. The first stem electrically and mechanically connects to the second stem. The second polarity terminal of the handle 28 abuts and biases against the second polarity terminal of the heater 33. The heater 30 can be made of metal, except for the ceramic plate and insulator elements.

After assembly of the heater to the handle, the heater can activate a heater coil element 38 that has heater air conduits 37 immediately adjacent to the heater coil element 38. The heater coil element 38 also includes a ceramic thermal insulator. Air that enters through the heater air intake openings 35 exits through the heater air conduits 37. The heater air intake openings 35 are disposed on an external surface of the heater, and approximately four openings can be formed or drilled on the external surface of the heater element. The heater air conduits 37 form a ring next to the heater coil element 38.

The cartridge housing 40 fits over the heater 30 and can connect to the heater at a heater threaded connection 36. The cartridge housing 40 may have internal threading that connects to the heater threaded connection 36. The cartridge housing has a cylindrical cartridge housing outside wall 41. The cartridge housing also includes a first cartridge housing O-ring seal groove 42 and a second cartridge housing O-ring seal groove 43. A pair of O-rings are installed on the pair of O-ring seal grooves to provide an airtight connection to the main body. The cartridge housing is hollow and tubular so that it defines a cartridge housing chamber 44. The cartridge housing can be made of metal.

The cartridge housing chamber 44 is enclosed between the heater and a cartridge housing lid 50. The cartridge housing lid 50 has a threaded connection to the cartridge housing. The cartridge housing lid 50 has a cartridge housing lid sidewall 51. The cartridge housing lid sidewall 51 has a cartridge housing lid threaded connection 52. Additionally, the cartridge housing lid 50 has a cartridge housing lid grille 53 that can be installed within the bounds of the cartridge housing lid sidewall 51. The cartridge housing lid grille 53 may be a small circular plate of metal and have small circular openings less than 1 mm in diameter and placed in a grid pattern.

The grille baffle plate 60 can fit over the cartridge housing lid 50 and placed between the main body and the cartridge housing lid 50. The cartridge housing lid grille 53 and the grille baffle plate 60 can have the same grid pattern of small circular openings. The grille baffle plate 60 has grille baffle plate apertures 62 that can also be located in a square or hexagonal grid pattern. The grille baffle plate 60 has a grille baffle plate rim 61 that forms a margin of unventilated area having no apertures. The margin of unventilated area is a sheet of thin stainless steel cut to a circular profile to match that of the main body cartridge housing cavity 81.

A regulator valve 70 has a regulator valve switch 71. The regulator valve switch 71 has a regulator valve secondary opening 72. The regulator valve 70 is inserted into the main body 80 at the main body regulator valve cavity 82. The regulator valve body fitting portion 74 has a regulator valve seal 73 that can be formed as an O-ring so that it seals to an inside surface of the main body regulator valve cavity 82. The regulator valve also has a regulator valve body narrow portion 75 that does not seal against the inside surface of the main body regulator valve cavity 84.

The regulator valve body narrow portion 75 is sized so that a conduit is allowed to flow through the main body from the main body cartridge housing cavity 81 to either of the pair of ports located on the main body mouthpiece mesa 89, namely the main body vapor outlet 86 and the main body secondary outlet 85. The regulator valve also has a regulator valve intake opening 76 that makes fluid communication to the regulator valve secondary opening 72 when the regulator valve switch 71 is depressed. The regulator valve secondary opening 72 can be formed as an opening located on the valve switch 71. The regulator valve intake opening 76 is preferably formed on the regulator valve body narrow portion 75.

The main body 80 has a main body cartridge housing cavity that receives the cartridge housing 40, cartridge housing lid 50, and the grille baffle plate 60. The main body 80 also has a main body regulator valve cavity 82 for receiving a regulator valve 70. The main body 80 takes airflow through the grille baffle plate 60 and through the cartridge housing lid grille 53. The main body 80 connects to the cartridge housing 40, to the regulator valve 70, and to the mouthpiece 90 at a main body mouth piece O-ring seal 84. The main body has a main body valve cavity air outlet 83 which leads to a main body vapor outlet 86. The main body also has a main body secondary outlet 85. The secondary outlet 85 is larger than the main body vapor outlet 86.

The main body further includes a mouthpiece. The mouthpiece 90 is preferably made of a transparent plastic injection molded member that has a mouthpiece flare 91. The mouthpiece flare 91 forms a mouthpiece rim 92. The mouthpiece 90 is substantially hollow to form a mouthpiece channel 93 within it. The mouthpiece 90 connects to the main body 80 at a main body sidewall 88 and the main body sidewall 88 has a main body mouth piece O-ring seal 84 that seals to an internal surface of the mouthpiece channel 93. The main body mouthpiece mesa 89 has a small main body vapor outlet 86 and a larger main body secondary outlet 85. The main body mouthpiece mesa 89 has a main body sidewall 88 which preferably has a main body mouthpiece O-ring seal groove for retaining the main body mouthpiece O-ring seal 84.

The mouthpiece channel 93 draws air to a user's mouth. The air from the mouthpiece channel 93 comes from the main body vapor outlet 86 that is located on the main body mouth piece mesa 89. The air also comes from the main body secondary outlet 85. A user can press the regulator valve switch 71 on the regulator valve 70. Pressing the regulator valve switch 71 opens the main body secondary outlet 85 to the ambient air. The main body secondary outlet 85 is in fluid communication with the regulator valve intake opening 76. When a user wishes to mix ambient air with vapor, the user can press the regulator valve switch 71 which draws ambient air through the regulator valve secondary opening 72, which passes ambient air through the regulator valve intake opening 76 for mixing in the main body regulator valve cavity 82. The mixture of ambient air and vapor then passes through the main body secondary outlet 85, and finally through the mouthpiece channel 93 to the user.

The sum of the cross sectional area of the heater air intake opening 35 should be smaller than the cross sectional area of the main body secondary outlet 85. The cross section area of the main body regulator valve cavity air outlet 83 should be smaller than the main body secondary outlet 85. The main body secondary outlet 85 passes through a top wall of the main body which is defined as the main body mouthpiece mesa 89. Similarly, the main body regulator valve cavity air outlet 83 passes through the top wall of the main body and exits as the main body vapor outlet 86.

The user can press the regulator valve intermittently, not at all, or continuously so that the user can control the precise concentration of the vapor being inhaled. Different users may prefer a rich or lean mixture of vapor and air. A user that is trying to quit smoking can start with a rich mixture and work toward a lean mixture to gradually taper off in nicotine usage. The mouthpiece is preferably of transparent plastic so that the user can see the vapor being inhaled. When a user wants to stop inhaling, the user can press the regulator valve and the column of vapor will break siphon and the vapor will purge outward through the heater air intake opening by virtue of density difference between supplemental ambient air and vapor.

The heater is preferably modularly removable. By making the heater a separate unit that is threaded attached and sealed by O-rings, it allows easy cleaning and easy replacement.

The above detailed description of the preferred embodiment is an example of an apparatus described by the following claims.

The invention claimed is:
1. A vapor inhaler comprising:
   a. a handle, wherein the handle contains a battery;
   b. a heater connected to the handle, wherein the heater has heater air intake openings for receiving air, and wherein the heater has heater air conduits for exhausting air, wherein the heater is modularly removable;
   c. a cartridge housing connected to the heater, wherein the cartridge housing has a cartridge housing lid and a cartridge housing lid grille mounted to the cartridge housing lid, wherein the cartridge housing produces vapor that passes through the cartridge housing lid grille;
   d. a main body connected to the cartridge housing, wherein the main body further includes a main body cartridge housing cavity, wherein the main body further includes a mouthpiece; and
   e. a regulator valve mounted to the main body, wherein the regulator valve has a regulator valve secondary opening that provides a supplemental ambient air supply when the regulator valve is in an open position, wherein the regulator valve does not provide a supplemental ambient air supply when the regulator valve is in a closed position, wherein the main body cartridge housing cavity exhausts to either of a pair of ports located on a main body mouthpiece mesa, namely a main body vapor outlet and a main body secondary outlet, wherein the heater air intake openings have a smaller cross sectional area than the main body secondary outlet, wherein the main body secondary outlet is larger than the main body vapor outlet.

2. The vapor inhaler of claim 1, wherein the regulator valve has a regulator valve secondary opening located on a regulator valve switch, wherein the regulator valve switch is formed as a pushbutton, wherein the regulator valve secondary opening is located on a sidewall of the pushbutton.

3. The vapor inhaler of claim 1, wherein the cartridge housing is mounted to fit within the main body cartridge housing cavity.

4. The vapor inhaler of claim 1, wherein the mouthpiece is detachable from the main body.

5. The vapor inhaler of claim 1, wherein the main body has the main body secondary outlet that has fluid communication to ambient air when the regulator valve is in open position; wherein the main body has the main body vapor outlet providing a flow of vapor.

6. The vapor inhaler of claim 1, wherein the main body further includes a main body regulator valve cavity, wherein the regulator valve is mounted to fit within the main body regulator valve cavity.

7. The vapor inhaler of claim 6, wherein the regulator valve has a regulator valve body narrow portion sized to provide a conduit of vapor flow through the main body from the main body cartridge housing cavity to the mouthpiece.

8. The vapor inhaler of claim 7, wherein the regulator valve has a regulator valve secondary opening located on a regulator valve switch, wherein the regulator valve switch is formed as a pushbutton, wherein the regulator valve secondary opening is located on a sidewall of the pushbutton.

9. The vapor inhaler of claim 7, wherein the cartridge housing is mounted to fit within the main body cartridge housing cavity.

10. The vapor inhaler of claim 7, wherein the mouthpiece is detachable from the main body.

11. The vapor inhaler of claim 7, wherein the main body has the main body secondary outlet that has fluid communication to ambient air when the regulator valve is in open position; wherein the main body has the main body vapor outlet providing a flow of vapor.

12. The vapor inhaler of claim 6, wherein the regulator valve has a regulator valve body fitting portion, wherein the regulator valve on a fitting portion has a regulator valve seal that is formed as an O-ring to seal against an inside surface of the main body regulator valve cavity.

13. The vapor inhaler of claim 12, wherein the regulator valve has a regulator valve secondary opening located on a regulator valve switch, wherein the regulator valve switch is formed as a pushbutton, wherein the regulator valve secondary opening is located on a sidewall of the pushbutton.

14. The vapor inhaler of claim 12, wherein the cartridge housing is mounted to fit within the main body cartridge housing cavity.

15. The vapor inhaler of claim 12, wherein the mouthpiece is detachable from the main body.

16. The vapor inhaler of claim 12, wherein the main body has the main body secondary outlet that has fluid communication to ambient air when the regulator valve is in open position; wherein the main body has the main body vapor outlet providing a flow of vapor.

* * * * *